US006962568B1

(12) United States Patent
Morger

(10) Patent No.: US 6,962,568 B1
(45) Date of Patent: Nov. 8, 2005

(54) MEASURING DEVICE FOR DETERMINING AN UNEVEN LOADING OF THE HUMAN BODY IN THE UPRIGHT POSITION

(76) Inventor: Otto Morger, Webergrasse 27, Rapperswil (CH) CH-8640

( * ) Notice: Subject to any disclaimer, the term of this patent is extended or adjusted under 35 U.S.C. 154(b) by 0 days.

(21) Appl. No.: 10/220,869

(22) PCT Filed: Mar. 5, 2000

(86) PCT No.: PCT/CH00/00246

§ 371 (c)(1),
(2), (4) Date: Sep. 5, 2002

(87) PCT Pub. No.: WO01/66009

PCT Pub. Date: Sep. 13, 2001

(30) Foreign Application Priority Data

Mar. 6, 2000 (CH) ..................... 431/00

(51) Int. Cl.⁷ .................. A61B 5/103; A61B 5/117
(52) U.S. Cl. .................................... 600/595
(58) Field of Search ..................... 600/587, 300, 600/594, 595; 33/515

(56) References Cited

U.S. PATENT DOCUMENTS 3,955,285 A * 5/1976 Moeckl .................. 33/515
4,033,329 A 7/1977 Gregory et al.
5,088,504 A 2/1992 Benesh et al.
5,443,079 A 8/1995 Greenawalt
5,823,974 A * 10/1998 Grassi ..................... 600/595

FOREIGN PATENT DOCUMENTS

| AT | 002 239 U1 | 3/1997 | |
| CH | 671330 | 8/1989 | |
| DE | 197 12 229 | 3/1997 | |
| FR | 2.070.280 | 11/1969 | |
| WO | WO 9500073 A1 * | 1/1995 | .......... A61B 5/103 |
| WO | WO 95/35083 | 12/1995 | |

* cited by examiner

Primary Examiner—Max F. Hindenburg
Assistant Examiner—Brian Szmal
(74) Attorney, Agent, or Firm—Speckman Law Group PLLC; Janet Sleath

(57) ABSTRACT

The present invention relates to a measuring device for determining an uneven loading of the human body in the upright position, comprising a base element with two balances, and an adjustment unit for positioning individual points or regions of the body of the person to be measured. The adjustment unit comprises two vertical struts fixed to a base element, on which measuring and fixing elements are arranged in a vertically displaceable manner. A first measuring and fixing element is provided for measuring and fixing the knee with a transverse edge for the sides of the feet, together with a second measuring and fixing element for measuring and fixing the hips, and a third measuring and fixing agent element for measuring and fixing the shoulder region, are provided.

14 Claims, 4 Drawing Sheets

MEASURING DEVICE FOR DETERMINING AN UNEVEN LOADING OF THE HUMAN BODY IN THE UPRIGHT POSITION

FIELD OF THE INVENTION

The present invention relates to a measuring device for determining an uneven or incorrect loading or posture of the human body in the upright position.

Humans with an incorrect upright posture load their musculoskeletal system irregularly and therefore suffer pain at various body locations. As known in the art, various devices are available for determining the incorrect posture.

BACKGROUND OF THE INVENTION

So-called hip spirit levels consist of a base body or a guiding member with two limbs or nibs pivotably movable therein, in which there are integrated, in each case, a spirit level or bubble tube. For determining the body posture the person to be measured must place himself upright in his natural posture. The person carrying out the diagnosis then from the rear holds the hip spirit level at the height of the hip onto the body. The pivotable limbs at the same time are placed on the hipbone on both sides. By way of the deviation of the bubble tube of the spirit level from the horizontal one may diagnose whether and to what extent the patient maintains the pelvis in an oblique presentation. Generally this oblique presentation is described as leg shortening, wherein this indeed is present in the form of a shorter leg or more often only appears to be, generally caused by an overstretching of muscles or ligaments. The cause of such an apparent leg shortening may be a knock or a short incorrect loading of the musculoskeletal system.

A hip spirit level for determining the leg shortening according to the above described state of the art is known from CH-A-671 '330.

The hip spirit level according to the state of the art has several disadvantages. The body, by way of the displacement of the pelvis, compensates for the oblique presentation. The hip spirit level therefore measures the oblique presentation, which has already been partly compensated, but not the effective incorrect loading of the pelvis and of the legs.

Furthermore, the patient in this situation rarely positions himself in his natural posture, so that the readings are not true. Furthermore the position of the hip bone may not be easily determined particularly with obese persons, so that the measurement often may not be carried out with due care and attention.

For this reason several measuring devices are known which directly determine the incorrect loading of the legs in which the patient in each case with one foot places himself on a measuring balance.

FR-A-2,491,754 describes such a device for determining leg shortening. The patient places each foot on a vertically movable plate, wherein from the front, abutment elements are pressed onto his knee and his pelvis. The different weight loading of the two plates is registered and the plates are mutually lifted or lowered until they register the same weight loading. The difference in height of the two plates then indicates the shortening of the leg.

U.S. Pat. No. 5,088,504 discloses a measuring device with which pelvis displacement and weight loading for each leg may be ascertained. The measuring device comprises a base and a vertical trunnion attached thereon. In the base are arranged two balances, which are provided with an abutment for the heels of the patient. A measuring element for determining the pelvis displacement is displaceably arranged on a vertical trunnion, wherein the measuring element comprises a vertical displacement rod for setting the height, and two horizontally displaceable abutment bars for measuring the pelvis. For measurements, the patient freely places himself on the base with his back to the vertical trunnion.

In U.S. Pat. No. 4,033,329 there is described a similar measuring device where, however, there is no positioning abutment for the heels. A reliable reproduction of the measurement is not possible with the lack of a reference point.

WO-A-95/35063 shows a measuring device with two balances and a vertical trunnion on which there are arranged two measuring and fixation elements, one for the pelvis and one for the shoulders. For measurement, the patient stands with his face to the vertical trunnion, with the balances having elements for positioning the heels.

From AT-U-002,239 there is known a measuring device for determining an incorrect loading of the human body which comprises a base element having two balances and an adjustment unit for positioning individual body points, or regions, of the person to be measured. The adjustment unit comprises a vertical trunnion arranged on the base element, on which trunnion fixation elements are arranged in a vertically displaceable manner, wherein a first fixation element is present for the fixation of the hips and a second fixation element is present for the fixation of the upper body. On the base element there is present an abutment for positioning the heels of the person to be measured. The balances may be calibrated absolutely with respect to a calibration value or relative to one another. Furthermore, a third fixation element is present for the fixation of the knee as well as a lateral abutment for the sides of the foot. The abutment for positioning the heels is arranged on the side which is proximal to the vertical trunnion, wherein the vertical trunnion forms a positioning axis for defining a middle body line of the person to be measured.

All these measuring devices have the disadvantage that the measurements yield insufficient data for an exact diagnosis, since with the more simple apparatus one does not take into account the posture of the whole body, and with the more advanced apparatus the deviations of the body posture are reduced to a two-dimensional pattern. Because of this, incorrect postures and shortenings may not be unambiguously detected since twisting or distortions are not taken into account. For example, a distortion of the pelvis leads to an incorrect posture of the ilium and of the femur. Since the previously known apparatus only detect two-dimensional deviations within the frontal plane, such a distortion incorrect posture would be diagnosed as a shortening or lengthening of the femur, although there is not present any length change of the femur. In the same manner this applies to distortion of the shoulder girdle.

The insufficient, two-dimensional base of data for diagnosis thus does not permit the necessary therapeutic measures to be correctly planned and carried out.

SUMMARY OF THE INVENTION

It is an object of the present invention to provide a measuring device for determining an incorrect loading of a human body in the upright position, which permits a simple but unambiguous detection of deviations in all spatial directions.

It is a further object of the present invention to make available a measuring device which may very simply be provided in combination with electrical, electronic or laserbased sensors and data detection and data transmission means and electronic data processing means.

These objects are achieved by a measuring device with a base element comprising two balances and with an adjustment unit for positioning individual body points or regions of the person to be measured, wherein the adjustment unit comprises second and third vertically displaceable fixation elements for fixing the hip and shoulder region, wherein each fixation element comprises displaceable transverse struts and sagittal rods displaceably fastened thereon, wherein on the base element there are present abutments for positioning the heels of the person to be measured, which define a rear frontal plane, characterised in that at least two vertical struts define a positioning axis for the definition of a middle body line of the person to be measured and carry the fixation elements which are measuring and fixation elements which permit the position of body points to be determined in the frontal, transversal and sagittal planes, wherein on the saggital rods along the rod axes there are attached displaceable measuring bars in a pivotingly movable manner, byway of which in cooperation with the transverse struts and the sagittal rods the position of a body point to be measured may be determined in a transversal plane defined by transverse struts and sagittal struts.

BRIEF DESCRIPTION OF THE FIGURES

In the drawings, there is shown one embodiment [example] of the subject-matter of the invention and this is explained in the subsequent description. The directional terms are used in the manner common with anatomy. [There are shown in]

DETAILED DESCRIPTION OF THE INVENTION

Figure 1:
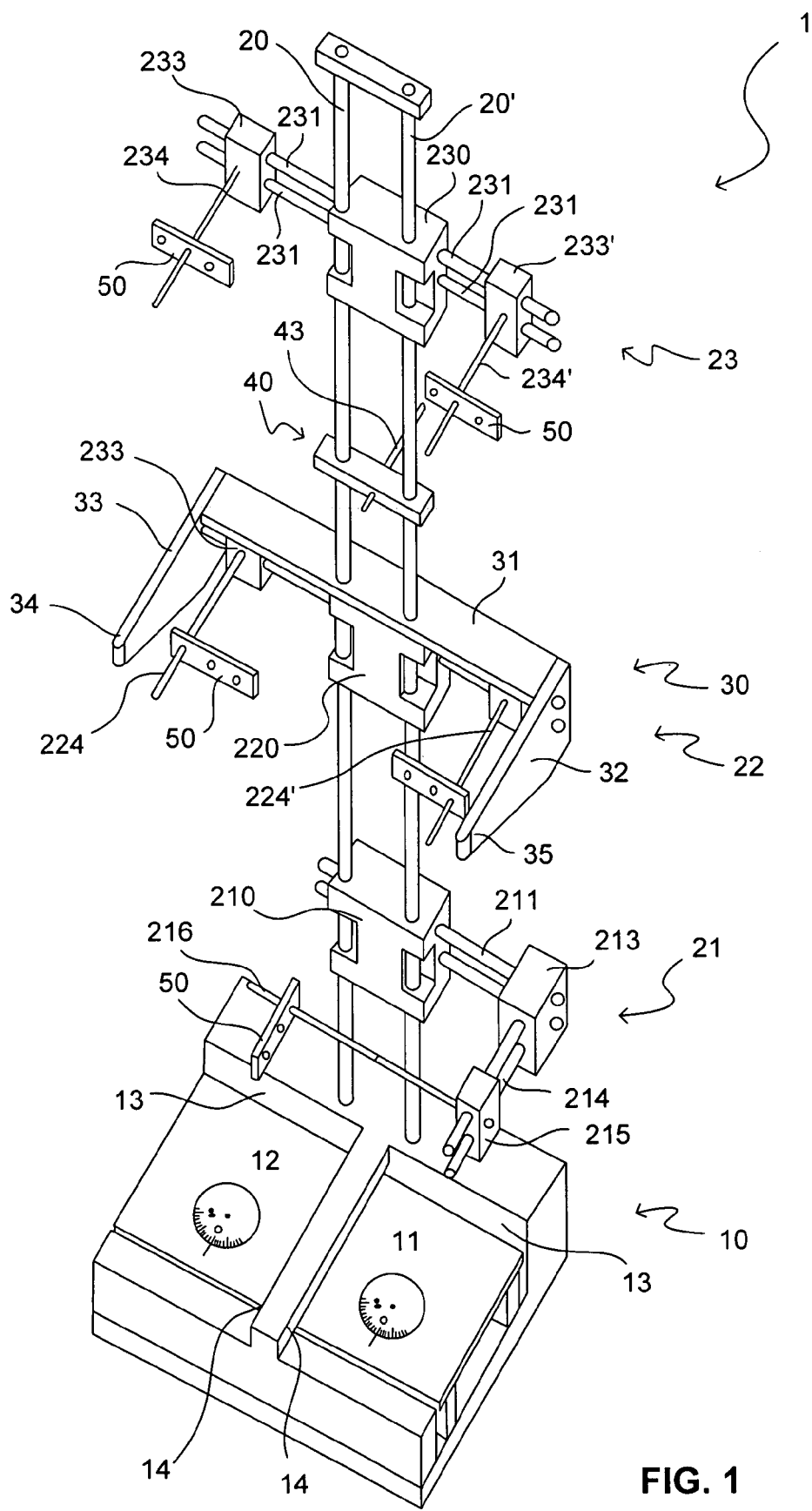
FIG. 1 illustrates a measuring apparatus in a view obliquely from the front.

The present invention permits a patient to stand in the natural posture during the measurement, with the complete body posture in a three-dimensional space being taken into account. The device according to the present invention comprises a positioning aid which at least approximately acts over the whole length of the body of the patient. This visual positioning aid is formed by at least two vertical trunnions on which, however, the patient does not lean. Advantageously there are arranged two or more, preferably three, vertically displaceable measuring elements on the vertical trunnions.

The measuring device according to the present invention comprises an adjustment unit by way of which the person to be measured may be fixed in an optimal position, quasi frozen, without his natural body posture being compromised. At the same time, the person to be measured is centered with respect to the vertical trunnion. In this position, by way of balances the different weight loading in the static center and, by way of the measuring elements the incorrect postures in the region of the legs, the hip and of the shoulder girdle, are measured. The device according to the present invention also permits, as will be explained hereinafter, for a test person to be measured in the free state. At the same time the person to be measured is fixed in a free, that is to say non-centered, position.

The double weight balances yield clear readings, by way of whose difference any present incorrect loading may be simply visualized in a manner which may be easily understood by the person carrying out the measurement.

Using the measuring device according to the present invention, as with the device already known by way of AT-U-002,239, one may ascertain whether the patient differently loads his right or left foot, that is to say the corresponding sides of the pelvis. The patient is relatively restricted, since he is accustomed to standing on a weight scale. Furthermore, the device according to the present invention permits the detection of twisting of the pelvis, shoulder girdle, head and spinal column. The degree of deviation of the shoulders with respect to the horizontal may be detected. In a preferred embodiment of the present invention, posture deviations of the legs (in colloquial terms bow legs or knock-knees) may be measured.

In a preferred embodiment the balances are removably arranged in the device. By way of this, several measuring steps may be carried out in order to completely measure out the body posture.

After a learning phase, the patient may carry out a few of the measurements himself without outside help. Since many incorrect body postures may be corrected without surgical operations but merely by way of special gymnastic exercises, an independent measurement is advantageous since the patient experiences a positive feedback which in turn supports the success of the therapy.

In order, however, to be able to measure a body exactly and completely, an operating person is necessary. Since the measurements are only to yield the basis for an exact diagnosis, the operating person must be taught to measure in an exact and reproducible manner, but he does not need to have particular medical skill.

In the accompanying drawings there is shown one embodiment of the subject matter of the present invention in detail, which is explained in the subsequent description.

The embodiment shown here comprises a base 10 with double weight balances 11, 12 and an adjustment and measuring unit 1.

The base 10 of the measuring apparatus has a right and a left weight scale 11, 12 which are arranged next to one another. The weight balances may be mechanical or electronic person balances of a known construction or of a special manufacture. Preferably, however, each balance shows the weight loading in absolute values, wherein it may be calibrated absolutely with respect to an independent calibration value. It is however also possible for only the difference of the weight loadings of the individual balance to be displayed in a common display. In this case it is sufficient for the balances to be able to be calibrated relative to one another. The calibration may be carried out at the place of manufacture, above all with relative calibrations as well as by the user himself. In a preferred embodiment the electronic balances are provided with an interface via which they may be connected to a central data collecting and evaluation unit. The collection, evaluation and visualization of the readings may, for example, be carried out with the help of special software on a personal computer. The data transmission may be carried out via cable. If this is not desirable or is of a hindrance, radio or infrared interfaces may be applied.

The two balances are advantageously arranged in a common housing in the base. In a preferred embodiment they are arranged individually or together in the device in a removable manner.

The base 10 comprises adjustment means for positioning in each case one foot of the person to be measured. In the illustrated embodiment there is a central abutment strip 14 running along the median plane and a rear abutment strip 13, which are to be contacted by the feet of the person to be measured. The lateral abutment strip 14 is arranged in the region between the two weight balances 10, 11. The abutment strip 14 is dimensioned such that the feet lie as close as possible to one another. Their width, and thus the distance between the feet, is 3–5 cm, preferably about 4 cm.

The above described double weight balance 11, 12 in this form is used for determining incorrect loadings of the human body. Since each foot stands on an independent balance, each balance shows the weight loading on the corresponding foot and thus on the corresponding side of the pelvis. With an incorrect posture, the two balances have different weight loadings, a fact which may be understood by the person taking the measurement. From the different weight loading, the apparent leg shortening of the patient may be determined with a simple calculating formula. Often the ascertaining of an incorrect loading is already sufficient. This measurement may be carried out and evaluated in a simple manner and may also be carried out by the patient himself.

For more exact measurements, the measuring device is provided with further measuring and adjustment means, which fix the position of individual body points or regions of the patient and thus ensure an exact and reproducible measurement.

The adjustment and measuring unit 2 consists of at least two parallel vertical struts 20 and 20', on which there are attached several measuring and fixation elements 21, 22, 23. In this embodiment, a total of three measuring and fixation elements are present for the partial fixation and measurement of three body regions. However, further regions may be measured and fixed wherein the measuring elements are essentially always constructed equally. Only the element 21 for measuring and fixing the thigh and knee region deviates from the basic construction.

The upright standing vertical struts 20, 20' are arranged on the base 10. The vertical struts 20, 20' define a rear plane which runs parallel to the frontal plane, and are approximately equidistant to the median plane. The vertical struts 20, 20' and also the fixation and measuring elements 21, 22, 23 are preferably manufactured of tubes. Furthermore, on the vertical struts 20, 20' there is attached at least one access clamp 30 whose rear horizontally running base element 31 carries two laterally projecting limbs 32, 33 which in each case may be provided with hand grips 34, 35. The access clamp 30 may be displaced in the vertical position along the struts 20, 20' and fastened in various vertical positions. The clamp 30 simplifies the mounting of the person to be measured onto the measuring apparatus 1, in the initial positioning phase, offers a secure hold and prevents him from seizing the measuring and fixing elements 22, 23 which would happen without the access clamp 30.

The first measuring element 21 primarily serves for the measurement and fixation of the leg and knee and is arranged between the base 10 and second measuring element 22 on the vertical struts 20, 20'. It comprises a base block 210 which is vertically displaceably held on the vertical struts 20, 20' and which carries a pair of rear transverse struts 211. The transverse struts 211 via an angle element 213 carry a second pair of lateral sagittal struts 214 which are arranged perpendicularly to the transverse struts, and which in turn, via an angle element 215, carry a frontal rod 216 arranged at a right angle to them. For reasons of stability, the struts 211 and 214 are advantageously designed as double tubes. The struts 211 and 214 and the rod 216 define and lie in a horizontal or transverse plane. The angle elements 213 and 215 are designed such that the sagittal strut 214 may be displaced transversally and the frontal rod 216 sagittally to the vertical struts 20, 20' within this horizontal plane. The displacement movability is limited by the length of the struts 211 and 214. The angle elements 213, 215 comprise means for locking the struts, or the frontal rod in a desired position. Struts 211, 214, as well as frontal rod 216, are provided with a scaling which permits the relative position of the angle elements 213, 215 on the struts 211, 214 to be determined sufficiently accurately. The scaling on the frontal rod serves for determining the position of measuring bars 50 which are yet to be described in more detail in the following.

In a preferred embodiment, the scaling may be visually read by the user. If the data is to be determined electronically in a direct manner, then the scaling may also be brought into a form which may be read electromagnetically. The angle elements are then provided with read means which determine the relative position of the angle element on the struts 211, 214. This measuring signal may, as already mentioned with the balance 11, 12, be transmitted further to a data collection unit via cable or without cable, and/or be represented on a display integrated in the angle elements 213, 215. The base block 210 is fixable at the desired height at any vertical position on the vertical struts 220, 20' by way of known locking means, such as screw and/or clamp connections.

Figure 2:
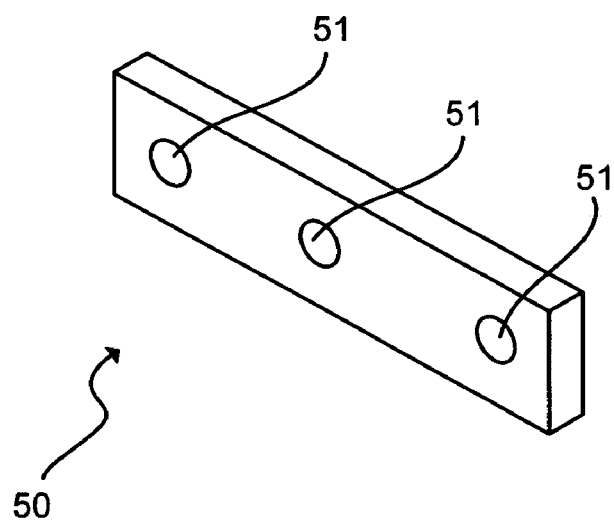
FIG. 2 illustrates a measuring bar in a view from the front.

The second fixation element, in contrast to the first fixation element 21, is bilaterally symmetrical to the median plane of the measuring apparatus 1. Analogously to the element 21, also with the element 22, a base block 220 held vertically displaceable on the vertical struts 20, 20' carries a pair of rear transverse struts 221. On both ends of the strut 221, there are again arranged displaceable angle elements 223, 223'. The angle elements in each case carry a sagittal rod 224, 224' projecting to the front. The sagittal rods are likewise provided with scalings as have already been described above and may, by way of the angle elements 223, 223' with known locking means, be fixed in their relative position to the vertical struts 20, 20'. On the sagittal struts, there is attached in each case at least one measuring plate 50 in a pivotingly movable and displaceable manner. In the simplest case, a measuring plate 50 consists of an elongate rectangular plate as shown in FIG. 2. In plate 50 at the ends and in the middle, there is incorporated in each case one bore 51. These bores are dimensioned such that the measuring plate may be displaced and pivoted on the sagittal rod 224 with a low resistance and at the same time, exerts sufficient clamping force in order to remain in each pivot position when an external force effect is not provided. The bars 50 are advantageously manufactured of plastic. The three bores 51, when required, permit the length of the plate available for measurement to be varied quickly and simply only by way of inserting from one hole 51 to the next. Of course, bars with one or two holes may also be applied.

The second measuring element 22 serves primarily for measuring and fixing the pelvis, and in the shown embodiment, is arranged between the first measuring element 21 and the access aid 30 on the vertical struts 20, 20'. Above the second measuring element 22, a known hip spirit level may be assembled on the vertical struts 20, 20'.

The third measuring and fixation element 23 serves for measuring and fixation of the upper body and is arranged above the access aid 30 on the vertical struts 20, 20'. It comprises essentially the same basic construction as the second measuring element 22, and is likewise provided with measuring bars 50. Since the measuring bars of the third measuring element, apart from measuring the distortion of the shoulder girdle, also serve for measuring the shoulder position, they are provided with an angle measurement means. From FIG. 4 it is evident how the deviation of the shoulder position with respect to the horizontal is determined. In the simplest case, a reference line may be attached on the sagittal rod and an angle scale on the measuring plate, by way of which the pivot angle of the measuring plate may be determined.

For measuring asymmetries of the head, in particular of the face and of the neck, the angle element 215 with a frontal rod 216 may be attached to a sagittal strut 234 or 234'.

Furthermore, between the vertical struts 20, 20', there is attached a further measuring element 40 which carries at least one measuring pin 43 for scoliosic measurement of the spinal column. The measuring pin 43 is transversally and sagittally displaceably held in a base block 41, which is displaceable in the vertical direction on the struts 20, 20'. The measuring pin is provided with a scaling so that the position of its tip with respect to the rear frontal plane defined by the rear abutment strip 13 may be measured. The deviation of the spinal column with respect to the median plane, in a preferred embodiment, may be determined directly by a pin 43 which is held vertically displaceable in or on the base block 41. This vertical displacement in the example shown in FIG. 1 is made possible by a carriage 42 which carries the dorsoventrally displaceable pin 43. A scaling on the base block 41 or carriage 42 permits the vertical displacement to be measured. A further measuring element 40' with a pin 43' may be arranged above the third measuring unit 23 on the vertical struts 20, 20'. With this, on the one hand the cervical spine and various parameters of the head posture and, on the other hand, also the body size may be determined.

At least one of the vertical struts 20, 20' is provided with a scale whose zero point lies in the standing plane formed by the scale balance. The scaling may be of the known optically readable type and/or electromagnetically coded. Analogously to the angle elements, the base blocks 210, 220, 230, 41 may also be equipped with digital reading displays as well as with interfaces for data transmission. The vertical position of the measuring units 21, 22, 23 and 40 may be determined quickly and precisely at any time. The base blocks 210, 220, 230 and 41 may be fixed by way of the known locking means in a certain vertical position on the vertical struts 20, 20'.

In the region of the second fixation element 22 for the hip, there is attached a hip spirit level in an embodiment form which is not shown here, as already described above. It consists, as with the known hip spirit level, of a slightly bent, rod-shaped base body and pivotable limbs arranged thereon on both sides. In the base body, there is contained at least one bubble tube for determining the position of the spirit level with respect to the horizontal. The limbs are preferably longer than those of the known hip spirit levels so that they may also project up to the front region of the hips with obese persons, although the hip spirit level is not pressed on the body of the patient. The hip spirit level is displaceably and lockably held, for example, above the second measuring element 22 on the vertical struts 20, 201. It may however also be arranged on the second base block 220 itself and be commonly displaceable with this.

Furthermore, in the uppermost region of the vertical struts 20, 20', there may be arranged a displaceable measuring bar for determining the body size wherein one uses the scale attached on the vertical struts. The measurement of the size serves, amongst other things, as the proof that the patient, after correction of the incorrect posture, stands more upright and thus appears larger.

In the following, the measuring procedure according to the present invention is described in more detail. A quick recording, which may be carried out by an experienced person in approx. 5 minutes, comprises, for example, the following steps:

For carrying out the measurement, the person to be measured stands with his back to the vertical struts 20, 20' freely on the base 10 or the double weight balance 11, 12. The right foot is placed on the right weight balance 12, and the left foot onto the left weight balance 11.

The measuring and fixation elements 21, 22, 23 are adapted to the size of the test person, and set to approximately knee, hip and shoulder height.

Figure 5:
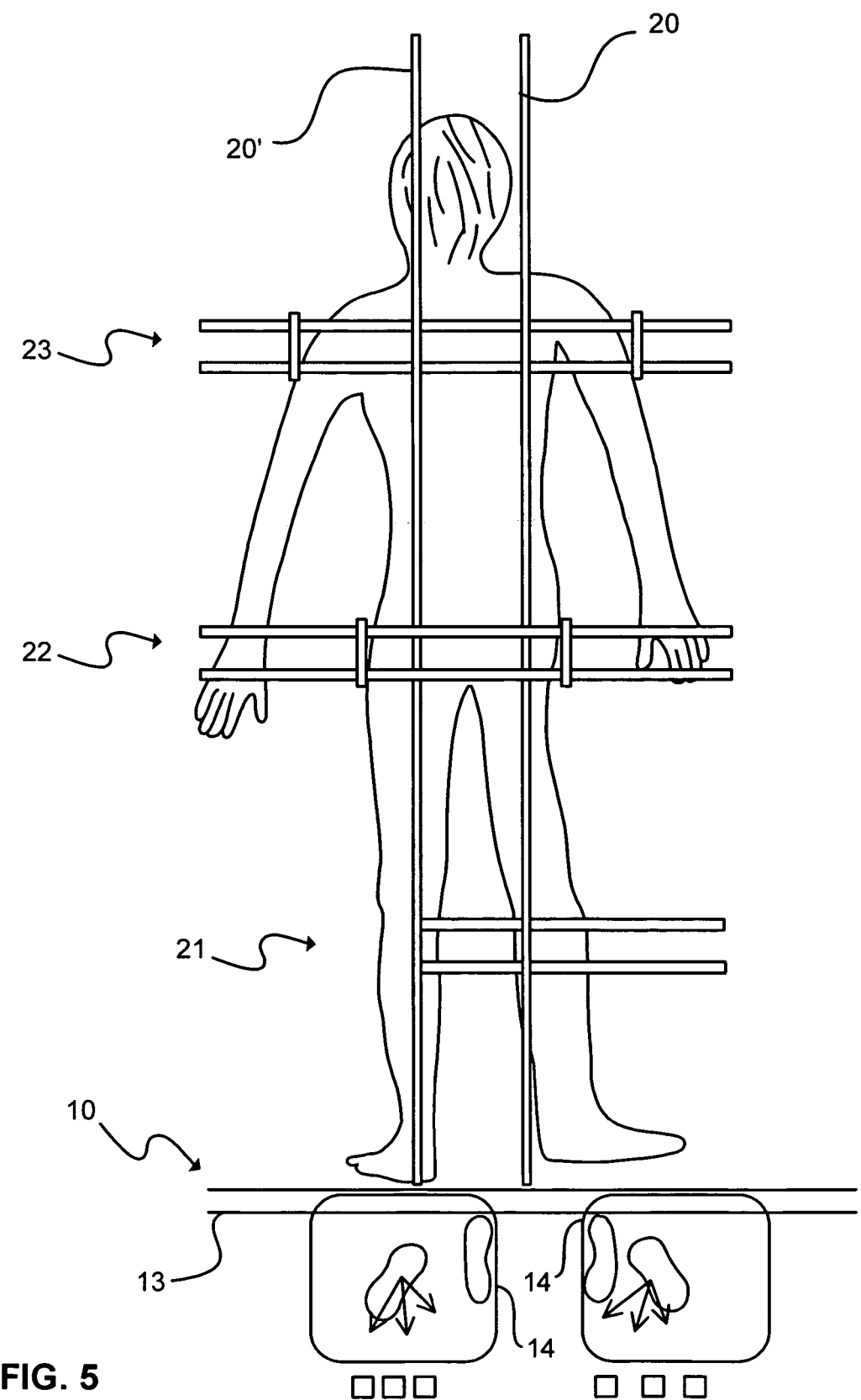
FIG. 5 illustrates a data page for recording the foot position of a test person in the free fixed state.

The foot position in the free state is as indicated in FIG. 5, and the rotation of the sole is measured. FIG. 5 is to be understood as a first data page of a series of data pages which may be used with an actual measurement for the written recording of the measuring results. The data pages simultaneously serve as a guide through a measurement, since they ensure that no measuring steps are forgotten.

From the free state, likewise as indicated in FIG. 5, the feet are positioned on the abutments 13, 14. Now the test person in this free position or posture is fixed by way of the sagittal struts 224, 224', 234', 234'. The test person, at the same time with the rear buttock and shoulder regions, contacts the base plates 220 and 230 or parts of the horizontal struts 221, 231 without having to center on a vertical strut.

Figure 4:
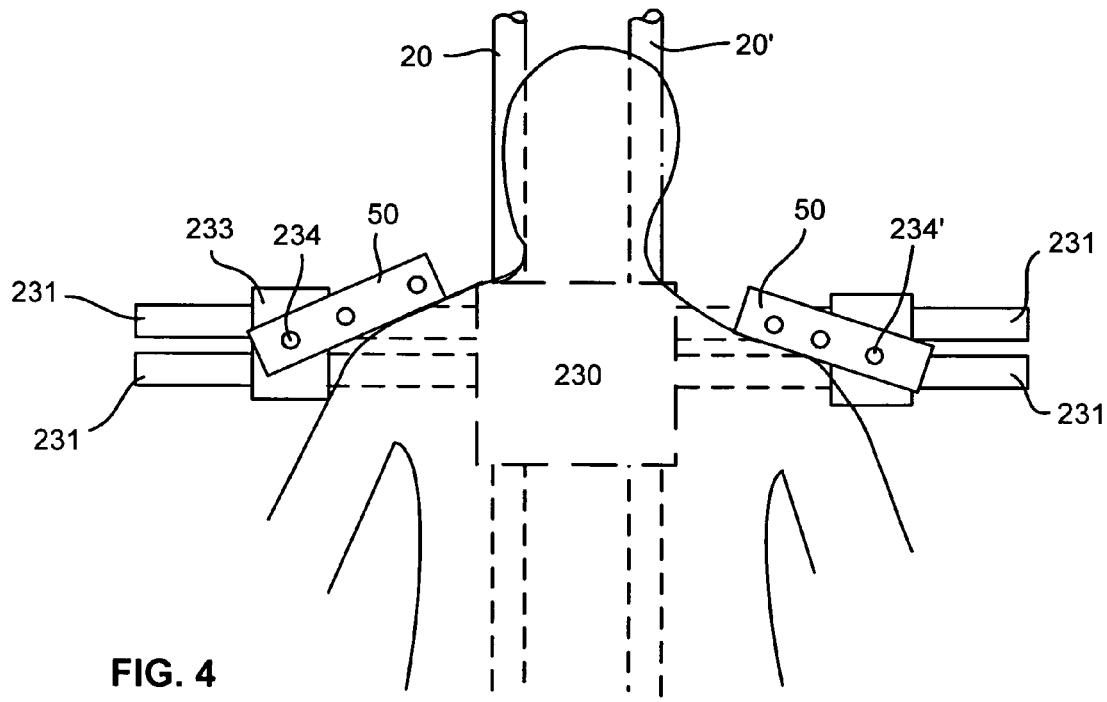
FIG. 4 illustrates a schematic section through the apparatus at the height of the third measuring element, wherein the shoulder region of a patient in the turned position is represented with a full line.

The lateral position of the hip is recorded;
the lateral position of the shoulders is recorded;
the leg print is read off from both balances;
the lateral deviation of the head position is measured;
the lateral deviation of the neck position is measured; and
the shoulder position is determined according to FIG. 4.

The shoulders and hips are centered, and the knees with the frontal rod of the first fixation element is fixed in an extended position. In this centered position, the pelvic obliquity may be measured. For this, a hip spirit level is fastened on the vertical struts 20, 20' above the second measuring element 22, and the apparent leg shortening is determined in the known manner.

In contrast to the above described quick or short recording, with a more detailed or "large" recording which lasts for approximately 15 minutes, considerably more measurements are carried out and more measuring points and dimensions are recorded. Initially, the test person stands freely in the measuring apparatus and the measurements are carried out as described above. Additionally, after these, the following measurements are advantageously also carried out.

Hand posture and foot length difference are determined.

For determining any crookedness of the legs, for example: bow legs; knock-knees; femoral deviation; knee deviation; and calf deviation, the measurement element 21 is displaced into the desired, knee, thigh or lower leg region. By way of the one or more measuring bars 50, which may be displaced on the frontal rod 216 and pivoted to the rear, the measure of the deviation from the median plane is measured on the inside and outside at the crus.

Figure 3:
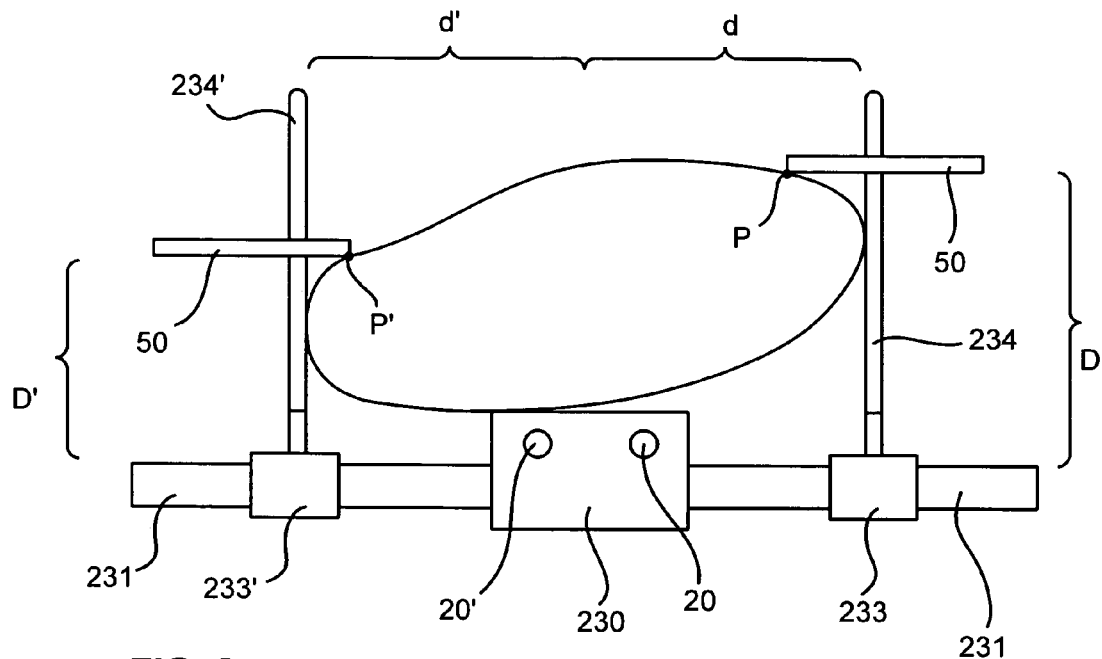
FIG. 3 illustrates measuring bars with the measurement of a shoulder part of a patient.

In further measurement, one determines the kneecap height, size, head posture, neck, shoulder blade below or at breast height, loins, buttocks, knee joint, knee joint deficit, plumb line ear-hip-malleolus, and/or shoulder rotation, as shown in FIG. 3. With this measurement, the measuring bars 50 on the sagittal rods 234, 234' are now applied. The distances D, D' of the measuring points to the rear frontal plane, which is defined by the abutment 13, are determined. This measurement, or these readings in combination with the values from the lateral positions of the saggital rods 234, 234' provide a correct base for determining the rotation of the shoulders. In the illustrated example, the conventionally determined lateral distances of the shoulders d, d' to the median plane are approximately identical. In the conventional measuring method with conventional apparatus, a rotation is recognised still by asymmetry. Only the application of the measuring bars 50 permits the rotation to be recognised and exactly measured.

For determining the pelvis rotation, the measuring bars 50 on the sagittal rods 224, 224' are used in an analogous manner. Pelvis posture and hand posture are determined. Furthermore, the foot is phaenologically assessed for the following abnormalities: claw toes; halux; splayfoot; flatfoot; ps valgus; and falt foot.

Now again, the shoulder and hips are centered and the knee beam 216 is applied in order to be able to measure the pelvic obliquity by way of a hip spirit level.

With any occurring pelvic obliquity, in the known manner, one lays a small plate under sole of the foot of the shorter leg. Advantageously, in each case for one or more measuring sequences, one prepares data recording pages into which the respective measuring results may be directly registered. As already mentioned, these data pages makes it easier for the unexperienced user to carry out the measurements in the correct sequence and prevent individual measurements from being forgotten. The readings may be evaluated by way of the pages and be used for the diagnosis, or they may also be inputted into a computer and processed further [here]. It is of course also possible to directly accommodate the data in a computer.

The device according to the present invention permits patients to ascertain incorrect postures themselves. The device thus permits the patient to determine and control advances in therapy himself or with the help of other persons. If, for example, in a long-term therapy one attempts to relieve muscle hardening which leads to incorrect postures, the patient himself may check the success of the therapy; and when the therapy is successful, he is not only informed by the positive feedback but he is also motivated into further therapy.

The rotation of the leg, the pelvis, the hip displacement and the pelvic elevation state create various evasive and compensation postures of the upper and lower body. With the two-dimensional measuring method known up to now, such rotations are measured as shortening of the leg although extremities or the bone of the leg are in no way shortened. Only the exact detection of the deviation along all three spatial axes with respect to a static middle point permits an exact diagnosis and a correct therapy based on this diagnosis.

What is claimed is:

1. A measuring device for determining an incorrect posture and/or uneven loading of a human body in an upright posture, comprising:
   (a) a base element comprising two weight balances, the base element being provided with at least one abutment for positioning heels of a person to be measured, wherein the at least one abutment defines a rear frontal plane; and
   (b) an adjustment unit for positioning individual body points or regions of a person to be measured, the adjustment unit comprising:
      (i) at least two vertical struts which define a positioning axis for the definition of a middle body line of the person to be measured; and
      (ii) a first vertically displaceable fixation element and a second vertically displaceable fixation element positioned on the at least two vertical struts for fixing a hip region and a shoulder region, wherein each of said first and second fixation elements comprises a first and a second displaceable transverse strut and a first and a second sagittal rod displaceably attached to said first and second transverse struts, and wherein a first and a second pivotable and displaceable measuring bar are provided on said first and second saggital rods,
   whereby the position of a body point to be measured may be determined in a transverse plane defined by the first and second transverse struts and the first and second sagittal rods.

2. A measuring device according to claim 1, wherein the adjustment unit further comprises a third vertically displaceable fixation element positioned on the at least two vertical struts for fixing and measuring a knee region, the third fixation element comprising at least one transverse strut, at least one sagittal rod displaceably fastened attached to said transverse strut, a frontal rod attached to said sagittal rod, and at least one displaceable measuring bar attached to the frontal rod in a pivotably movable manner.

3. A measuring device according to any one of claims 1 and 2, wherein each of said transverse struts is held displaceably on said vertical struts by a base block and each of said sagittal rods is held displaceably on said transverse struts by an angle element.

4. A measuring device according to claim 1, wherein each of said measuring bars is provided with at least one terminal bore for receiving the saggital rod.

5. A measuring device according to claim 2, wherein the at least one measuring bar is provided with a terminal bore for receiving the saggital rod.

6. A measuring device according to any one of claims 4 and 5, wherein the at least one terminal bore is surrounded by an angle scale, and wherein each of said saggital rods is provided with a reference line.

7. A measuring device according to claim 2, wherein a length scale is provided on at least one of the vertical struts, at least one of the saggital rods and the frontal rod.

8. A measuring device according to claim 7, wherein the length scale may be read visually.

9. A measuring device according to claim 7, wherein the length scale may be read electromagnetically.

10. A measuring device according to claim 7, wherein each of said transverse struts is held displaceably on said vertical struts by a base block, and wherein the base block is provided with a reading means for reading off the length scales, the means being selected from the group consisting of: optical means; and electronic means.

11. A measuring device according to claim 7, wherein each of said sagittal rods is held displaceably on said transverse struts by an angle element, and wherein the angle element is provided with a reading means for reading off the length scales, the means being selected from the group consisting of: optical means; and electronic means.

12. A measuring device according to claim 1, wherein an access aid is movably attached to the vertical struts in a region above the first fixation element.

13. A method for determining an incorrect loading of a human body using a measuring device according to claim 1, comprising:
- a) positioning the feet of a freely standing test person on the abutments;
- b) fixing the hip and shoulder regions of the test person by means of the sagittal rods; and
- c) measuring rotation in the hip and shoulder regions by means of measuring points which are determined using the measuring bars.

14. A method for determining an incorrect loading of a human body using a measuring device according to claim 1, comprising:
- a) positioning the feet of a freely standing test person on the abutments;
- b) fixing the hip and shoulder regions of the test person by means of the sagittal rods; and
- c) determining a deviation of the spinal column with respect to a median plane by means of a pin.

\* \* \* \* \*

UNITED STATES PATENT AND TRADEMARK OFFICE
CERTIFICATE OF CORRECTION

PATENT NO. : 6,962,568 B1 Page 1 of 1
DATED : November 8, 2005
INVENTOR(S) : Otto Morger It is certified that error appears in the above-identified patent and that said Letters Patent is hereby corrected as shown below:

<u>Title page,</u>
Item [22], PCT Filing Date, should read -- May 3, 2000 --.

Signed and Sealed this

Fourteenth Day of March, 2006

JON W. DUDAS
*Director of the United States Patent and Trademark Office*